(12) United States Patent
Yamanishi et al.

(10) Patent No.: US 11,053,472 B2
(45) Date of Patent: Jul. 6, 2021

(54) BUBBLE-JETTING CHIP, LOCALIZED ABLATION DEVICE AND LOCALIZED ABLATION METHOD, AND INJECTION DEVICE AND INJECTION METHOD

(71) Applicant: JAPAN SCIENCE AND TECHNOLOGY AGENCY, Kawaguchi (JP)

(72) Inventors: Yoko Yamanishi, Tokyo (JP); Yohei Hamano, Tokyo (JP); Takuya Kambayashi, Tokyo (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 15/512,618

(22) PCT Filed: Sep. 29, 2015

(86) PCT No.: PCT/JP2015/077526
§ 371 (c)(1),
(2) Date: Mar. 20, 2017

(87) PCT Pub. No.: WO2016/052511
PCT Pub. Date: Apr. 7, 2016

(65) Prior Publication Data
US 2017/0306284 A1    Oct. 26, 2017

(30) Foreign Application Priority Data

Sep. 30, 2014 (JP) ............................. JP2014-201440

(51) Int. Cl.
*C12M 1/42* (2006.01)
*B05B 17/06* (2006.01)
(Continued)

(52) U.S. Cl.
CPC ............. *C12M 35/04* (2013.01); *A61B 18/14* (2013.01); *B05B 17/0607* (2013.01);
(Continued)

(58) Field of Classification Search
CPC combination set(s) only.
See application file for complete search history.

(56) References Cited

U.S. PATENT DOCUMENTS 6,913,605 B2 * 7/2005 Fletcher ............. A61B 17/3203
606/13
2005/0048651 A1    3/2005 Ryttsen et al.
(Continued)

FOREIGN PATENT DOCUMENTS

EP    1550556 A1    7/2005
JP    2006-508663 A    3/2006
(Continued)

OTHER PUBLICATIONS

EPO Translation JPWO2013129657. Aug. 9, 2018, pp. 1-27 (Year: 2018).*
(Continued)

*Primary Examiner* — Arthur S Leonard
(74) *Attorney, Agent, or Firm* — Amster, Rothstein & Ebenstein LLP

(57) ABSTRACT

The present invention enables fabrication and mass production of a bubble-jetting chip that includes a desired number of bubble jetting portions of the same size having bubble-jetting outlets of the same size.
Mass production is enabled by fabricating a bubble-jetting chip comprising a substrate and a bubble-jetting portion formed on the substrate, the bubble-jetting portion comprising: an electrode that is formed of a conductive material; an insulating portion that is formed of an insulating photosensitive resin, is provided so as to sandwich the electrode, and
(Continued)

includes an extended section that extends beyond the tip of the electrode; and a space that is formed between the extended section of the insulating portion and the tip of the electrode.

15 Claims, 11 Drawing Sheets

(51) Int. Cl.
      *A61B 18/00*     (2006.01)
      *C12N 13/00*     (2006.01)
      *C12N 15/89*     (2006.01)
      *A61B 18/14*     (2006.01)

(52) U.S. Cl.
    CPC ............ *C12M 35/00* (2013.01); *C12M 35/02* (2013.01); *C12N 13/00* (2013.01); *C12N 15/89* (2013.01); *A61B 2018/00577* (2013.01); *A61B 2018/00964* (2013.01)

(56) References Cited

U.S. PATENT DOCUMENTS

| | | |
|---|---|---|
| 2006/0017782 A1 | 1/2006 | Nishi et al. |
| 2006/0115888 A1 | 6/2006 | Gamelin et al. |
| 2015/0011930 A1 | 1/2015 | Yamanishi et al. |

FOREIGN PATENT DOCUMENTS

| | | |
|---|---|---|
| JP | 2007090135 A | 4/2007 |
| JP | 2008-509709 A | 4/2008 |
| JP | 2010022360 A | 2/2010 |
| JP | 2010506136 A | 2/2010 |
| JP | 5526345 B2 | 4/2014 |
| WO | 2013129657 A1 | 9/2013 |

OTHER PUBLICATIONS

Pavesi et al., How to embed three-dimensional flexible electrodes in microfluidic devices for cell culture applications. Lab Chip, 2011, 11:1593-1595 (Year: 2011).*

Korean Patent Office, Office Action in Korean Application No. 10-2017-7005866 (5 pp., 4 pp. English Translation), dated Mar. 2, 2018.

Takahiro Kaji, et al., Nondestructive micropatterning of living animal cells using focused femtosecond laser-induced impulsive force, AIP | Applied Physics Letters, Jul. 13, 2007, vol. 91, No. 023904, AIP Publishing.

Daniel Palanker, PhD, et al., Anterior capsulotomy with a pulsed-electron avalanche knife, J Cataract Refract Surg, Jan. 2010, vol. 36:127-132, Elsevier Inc.

Hiroki Kuriki, et al., Local Ablation of a Single Cell by Micro/nano Bubble, Proceedings of the 2012 JSME Conference on Robotics and Mechatronics, May 27-29, 2012, No. 12-3, 1A2-V05, The Japan Society of Mechanical Engineers, Hamamatsu, Japan.

Sou Takasawa, et al., Bio application by electrically induced bubble interface, Proceedings of the 61st Japan Society of Applied Physics Spring Meeting, Mar. 2014, p. 08-148, 19p-F2-11, The Japan Society of Applied Physics, Sagamihara, Japan.

Yoko Yamanishi, Local Ablation of a Single Cell by Electrically-induced Microbubbles, Journal of the Japan Society of Mechanical Engineers, Jul. 2014, vol. 117, No. 1148:28-30, Tokyo, Japan.

Takuya Kambayashi, et al., Two-dimensional reagent-laden bubble injection by arrayed electrodes, Proceedings of the 6th International Symposium on Micro-Nano Science and Technology of the Japan Society of Mechanical Engineers, Oct. 20, 2014 (2 pgs.), The Japan Society of Mechanical Engineers, Matsue, Japan.

Yohei Hamano, et al., Development of Dispensing Multiple Membranes-Laden Micro-bubbles, Journal of the Society for Chemistry and Micro-Nano System, Mar. 31, 2015, vol. 14, No. 1:35-36, ISSN 1881-364X, Tokyo, Japan.

International Searching Authority (ISA), Written Opinion of the International Searching Authority, for International Application No. PCT/JP2015/077526 (5 pp., 6 pp. English translation ), dated Jan. 12, 2016.

Y. Yamanishi, Drug/cell transport via gas/liquid interface of microbubbles, 2013 Special Education/Research Report, Shibaura Institute of Technology, Jun. 30, 2014, pp. 59-62, ISSN 2185-7326, Tokyo, Japan.

State Intellectual Property Office of People's Republic of China, First Office Action and First Examination Opinion Notice for Chinese Application No. 201580048277.4 (6 pp., 6 pp. English translation), dated Aug. 3, 2018.

Chao Yang, et al., Synthesis of Low Viscosity, Fast UV Curing Solder Resist Based on Epoxy Resin for Ink-Jet Printing, Journal of Applied Polymer Science, Jul. 5, 2013, pp. 187-192, vol. 129, Issue 1, Wiley Online Library, New Jersey.

State Intellectual Property Office of People's Republic of China, First Office Action and First Examination Opinion Notice for Chinese Application No. 201580048277.4 (6 pp., 6 pp. English translation), dated Aug. 3, 2018. [Please Note: This is a Resubmission of this reference, first submitted Sep. 6, 2018, because the last 3 pages of the reference translation were inadvertently omitted in the previous filing.].

Hiroki Kuriki, et al., Local Ablation of a Single Cell Using Micro/Nano Bubbles, Journal of Robotics and Mechatronics, Jun. 20, 2013, pp. 476-483, vol. 25, No. 3, Fuji Technology Press Ltd., Japan.

European Patent Office, Extended European Search Report, issued in European Patent Application No. 15 847 462.7 which is a European counterpart of patent family of U.S. Appl. No. 15/512,618 dated Oct. 26, 2017, 9 pages.

Federal Service for Intellectual Property (ROSPATENT), Official Action for Russian Federation Application No. 2017107150 (8 pp., 4 pp. English Translation), dated Nov. 1, 2017.

Japanese Patent Office, Office Action in Japanese Application No. 2016-552066 (3 pp., 2 pp. English Translation), dated Dec. 12, 2017.

Chao Yang, et al., Synthesis of Low Viscosity, Fast UV Curing Solder Resist Based on Epoxy Resin for Ink-Jet Printing, Journal of Applied Polymer Science, Jul. 5, 2013, pp. 187-192, vol. 129, Issue 1, Wiley Online Library, New Jersey. (Abstract only.).

European Patent Office, Office Action issued in European Patent Application No. 15847462.7, 4 pp., dated Sep. 10, 2019.

China National Intellectual Property Administration, Second Office Action for Chinese Application No. 201580048277.4 (5 pp., 8 pp. English translation), dated Nov. 21, 2019.

Chao Yang, et al., Synthesis of Low Viscosity, Fast UV Curing Solder Resist Based on Epoxy Resin for Ink-Jet Printing, Journal of Applied Polymer Science, Nov. 4, 2012, DOI: 10.1002/App.38738, pp. 187 to 192, John Wiley & Sons, Inc.

State Intellectual Property Office of People's Republic of China, Rejection Decision for Chinese Application No. 201580048277.4 (4 pp., 5 pp. English Translation), dated Jun. 28, 2020.

* cited by examiner

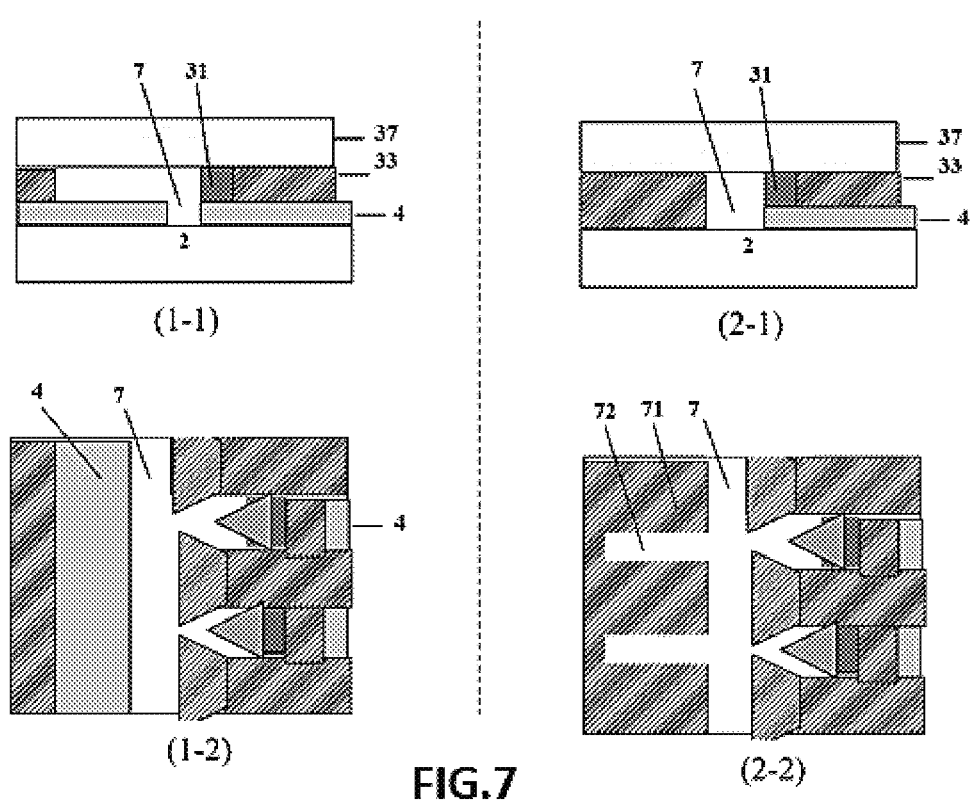
FIG.7
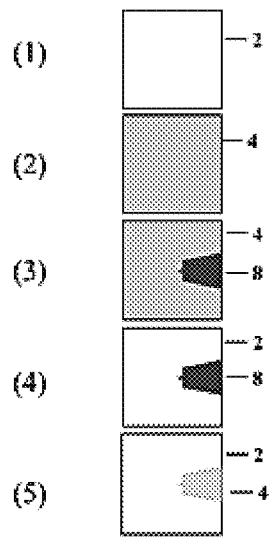 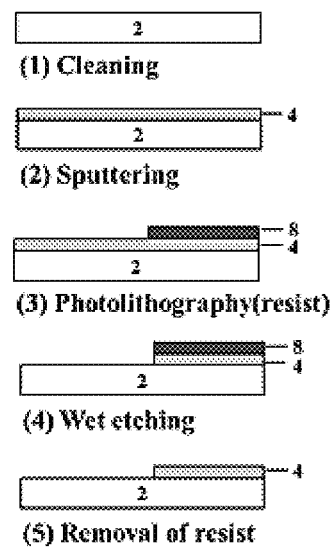
FIG.8-1

(1)

(2)

(1) (2)

(1) (2)

BUBBLE-JETTING CHIP, LOCALIZED ABLATION DEVICE AND LOCALIZED ABLATION METHOD, AND INJECTION DEVICE AND INJECTION METHOD

BACKGROUND OF THE INVENTION

Field of the Invention

The present invention relates to a bubble-jetting chip, a localized ablation device and localized ablation method, and an injection device and injection method, and particularly relates to a mass-producible bubble-jetting chip in which a desired number of bubble-jetting portions can be formed on a substrate and the size of bubble-jetting outlets can be reliably controlled, as well as a localized ablation device, localized ablation method, injection device, and injection method that include the bubble-jetting chip.

Description of the Related Art

Advances in biotechnology witnessed in recent years have been accompanied by increasing demand for localized processing of cells and the like, involving making a hole in a cell membrane or wall, and removing the nucleus from the cell, or introducing DNA or other nucleic acid substance into the cell. Methods employing a localized process techniques (herein sometimes referred to as "localized ablation methods"), such as contact process techniques using a probe, such as an electric scalpel or the like, or non-contact ablation techniques employing lasers or the like, are widely known. In particular, as a contact process technique using an electric scalpel, there has recently been proposed a technique for keeping the cauterization surface to one on the order of several microns, thereby minimizing the thermal invasion area and improving the resolution performance (see Non-patent Document 1).

Additionally, in the area of laser process, there have been notable breakthroughs in femtosecond lasers, and techniques for performing cell process (see Non-patent Document 2) and laser process techniques that minimize generation of bubbles in the liquid phase have been recently proposed.

However, in conventional contact process techniques employing a probe such as an electric scalpel, there was a tendency for the target to be burned away due to Joule heat generated by continuous high frequencies, resulting in significant roughness at the incision face and in surrounding tissue being significantly affected by thermal invasion due to heat. Also, in the non-contact process techniques using femtosecond lasers and other lasers, a problem has been presented in regard to the effect of thermal invasion of tissues surrounding the incision face by local impact of high-density energy.

Meanwhile, electroporation, sonoporation techniques employing ultrasound, particle gun methods, and the like are widely known as localized physical injection techniques (injection methods) for introducing nucleic acid substances or the like into cells or the like.

However, in conventional electroporation techniques, depending on the electrical field strength, there are limits as to how much permeability of the cell membrane can be improved, making it difficult to inject targets having stiff cell membranes or cell walls, instead of pliable lipid bilayer membranes; and due to restrictions regarding electrode placement and the like, localized injection at the intended site was difficult. Moreover, in sonoporation techniques employing ultrasound, it was difficult to focus the ultrasound, making it difficult to generate localized cavitation of bubbles and increase the resolution. In injection methods that rely on the particle gun method as well, the problem of low efficiency of introduction, due to separation of the substance deposited on the particle surface occurring when the particle is shot in was encountered. Additionally, the electroporation, sonoporation, and particle gun methods consume large amounts of substances for injection, making injection of costly substances difficult.

In order to solve the problems of the conventional localized ablation methods and injections described above, the present inventors discovered that cutting (localized ablation) of a process target can be performed by: producing a bubble-jetting member comprising a core that is formed of a conductive material, a shell part that is formed of an insulating material, covers the core, and includes a section extending from the tip of the core, and a space that is formed between the extended section of the shell part and the tip of the core; immersing the bubble-jetting member in a solution; applying a high-frequency voltage to the solution to produce bubbles; and continuously ejecting the bubbles into the process target. An application for patent was thus filed (see Patent Document 1).

The inventors also discovered that bubbles in which a solution of dissolved and/or dispersed injection material is adsorbed on the interfaces thereof can be produced by providing an outside shell part on the outside of the shell part of the bubble-jetting member so as to leave a space therebetween, and introducing a solution of dissolved and/or dispersed injection material into the space; and a process target can be cut and the injection material contained in the solution covering the bubbles can be injected into the process target by continuously ejecting the bubbles onto the process target. An application for patent was thus filed (see Patent Document 1).

PRIOR ART DOCUMENTS

Patent Documents

[Patent Document 1] Japanese Patent 5526345

Non-Patent Documents

[Non-Patent Document 1] D. Palanker et al., J. Cataract. Surgery, 38, 127-132 (2010)
[Non-Patent Document 2] T. Kaji et al., Applied Physics Letters, 91, 023904 (2007)

SUMMARY OF THE INVENTION

Problem to Be Solved by the Invention

However, the bubble-jetting member and gas/liquid jetting member described in Patent Document 1 are produced by heating and pulling the conductive core and the insulating member apart. A problem is accordingly presented in that it is difficult for the sizes of the bubble-jetting outlets for each of the bubble-jetting member and gas/liquid jetting member to be precisely arranged, and mass production is difficult.

Also, injection into a process target is often done into a plurality of locations in a single action rather than into a single location. However, with the bubble-jetting member and gas/liquid jetting member described in Patent Document 1, because it is difficult for the sizes of each of the bubble-jetting outlet of each bubble-jetting member and gas/liquid jetting member to be arranged precisely, as mentioned above, a problem is presented in that the quantity injected is not readily made uniform when a plurality of conventional bubble-jetting members and gas/liquid jetting members are combined.

Furthermore, although the outer periphery of the bubble-jetting member described in document 1is covered by the insulating shell part and the outer periphery of the gas/liquid jetting member is covered by the outside shell part, the size is not constant because the shell part and the outside shell part also are produced by heating and pulling apart the insulating material. Therefore, a problem is presented in that the combining operation is difficult due to the varying sizes. Another problem is presented in that the tips of the bubble-jetting member and the gas/liquid jetting member are very fragile, and therefore the operation of combining separately produced bubble-jetting members and gas/liquid jetting members is difficult.

The present invention was contrived in order to solve the abovementioned problems. After thoroughgoing research, it was newly discovered that: by using photolithography (1) a bubble-jetting chip that includes a desired number of bubble-jetting portions of the same size having bubble-jetting outlets of the same size could be fabricated and mass produced; (2) a bubble-jetting outlet can be formed using a photosensitive resin by sandwiching an electrode formed of a conductive material inside the photosensitive resin and forming the photosensitive resin extending from the electrode; and (3) forming a channel for delivering a solution containing an injection material on the bubble-jetting outlet side of the bubble-jetting portion makes it possible for bubbles in which the solution containing the injection material is adsorbed on the interfaces thereof to be continuously jetted at the process target, the process target to be cut, and the injection material contained in the solution covering the bubbles to be injected into the process target.

In other words, an object of the present invention is to provide a bubble-jetting chip, a localized ablation device and localized ablation method, and an injection device and injection method.

Means for Solving the Problems

The present invention relates to a bubble-jetting chip, a localized ablation device and localized ablation method, and an injection device and injection method as illustrated below.

(1) A bubble-jetting chip, comprising:
a substrate and a bubble-jetting portion formed on the substrate;
the bubble-jetting portion comprising:
an electrode that is formed of a conductive material;
an insulating portion that is formed of an insulating photosensitive resin, is provided so as to sandwich the electrode, and includes an extended section that extends beyond the tip of the electrode; and
a space that is formed between the extended section of the insulating portion and the tip of the electrode.

(2) The bubble-jetting chip according to (1) above, wherein the extended section is tapered.

(3) The bubble-jetting chip according to (1) or (2) above, wherein the photosensitive resin is a negative photoresist.

(4) The bubble-jetting chip according to any of (1) to (3) above, wherein two or more of the bubble-jetting portions are formed.

(5) The bubble-jetting chip according to any of (1) to (4) above, wherein an assist channel is formed in the insulating portion.

(6) The bubble-jetting chip according to any of (1) to (5) above, further comprising an energizing portion that is connected to the electrode.

(7) The bubble-jetting chip according to any of (1) to (6) above, wherein a counter electrode that constitutes an electrode pair with the electrode of the bubble-jetting portion is formed on the substrate.

(8) The bubble-jetting chip according to any of (1) to (7) above, wherein a channel for delivering a solution containing an injection material is formed on the space side of the bubble-jetting portion.

(9) A localized ablation device, comprising the bubble-jetting chip according to any of (1) to (8) above.

(10) An injection device, comprising the bubble-jetting chip according to any of (1) to (8) above.

(11) A localized ablation method, comprising:
injecting a solution so that a counter electrode has continuity with the electrode of the localized ablation device according to (9) above;
applying high-frequency pulses to an electrode pair configured with the electrode of the localized ablation device and the counter electrode to cause bubbles to be ejected from the tip of the bubble-jetting portion; and
processing a process target with the bubbles.

(12) An injection method, comprising:
injecting a solution so that a counter electrode has continuity with the electrode of the injection device according to (10) above;
delivering a solution containing an injection material to the front of the bubble-jetting portion;
applying high-frequency pulses to an electrode pair configured with the electrode of the injection device and the counter electrode to cause the ejection of bubbles onto which the solution containing the injection material is adsorbed; and
introducing the injection material into a process target while localized ablation is performed on the process target with the bubbles.

Effects of the Invention (1) In the present invention, use of photolithography makes it possible for a desired number of bubble-jetting portions of the same size having bubble-jetting outlets of the same size to be formed on a substrate. Accordingly, any discrepancy in the manufacture of individual bubble-jetting chips can be reduced.

(2) Bubbles of the same size can be jetted on a plurality of locations when localized ablation or local injection is simultaneously performed on a plurality of locations of a single process target. Also, the sizes of the bubble-jetting outlets of the bubble-jetting portions on a single bubble-jetting chip 1 can be varied, and bubbles of different sizes can be jetted on a plurality of locations of a process target.

(3) Unlike conventional production methods in which a core and an insulating material are heated and pulled apart, the bubble-jetting chips are formed using photolithography, which makes mass production possible.

(4) Forming a channel for delivering a solution containing an injection material on the bubble-jetting outlet side of the bubble-jetting portion facilitates continuous jetting of bubbles in which the solution containing the injection material is adsorbed on the interfaces thereof, and enables a process target to be cut and the injection material contained in the solution covering the bubbles to be injected into the process target.

BRIEF DESCRIPTION OF THE DRAWINGS

FIG. 4(1) is the entirety of the bubble-jetting chip 1, and FIG. 4(2) is an enlargement of the vicinity of the bubble-jetting portion 3;

FIG. 7(1-1) is a cross-sectional view of one example of the bubble-jetting chip 1 for injection, FIG. 7(1-2) is a top view of the same, FIG. 7(2-1) is a cross-sectional view of another example of the bubble-jetting chip 1 for injection, and FIG. 7(2-2) is a top view of the same;

FIG. 10(1) is a photograph of the bubble-jetting chip 1 produced in example 1, and FIG. 10(2) is a photograph showing the vicinity of the bubble-jetting portion enlarged;

FIG. 11(1) is a photograph of the bubble-jetting chip 1 produced in example 2, and FIG. 11(2) is a photograph showing the vicinity of the bubble-jetting portion enlarged;

FIG. 13(1) is a photograph of the bubble-jetting chip 1 produced in example 4, and FIG. 13(2) is a photograph showing the vicinity of the bubble-jetting portion enlarged.

DESCRIPTION OF THE PREFERRED EMBODIMENTS

The bubble-jetting chip, localized ablation device and localized ablation method, and injection device and injection method of the present invention are described in detail below with reference to the accompanying drawings.

Figure 1:
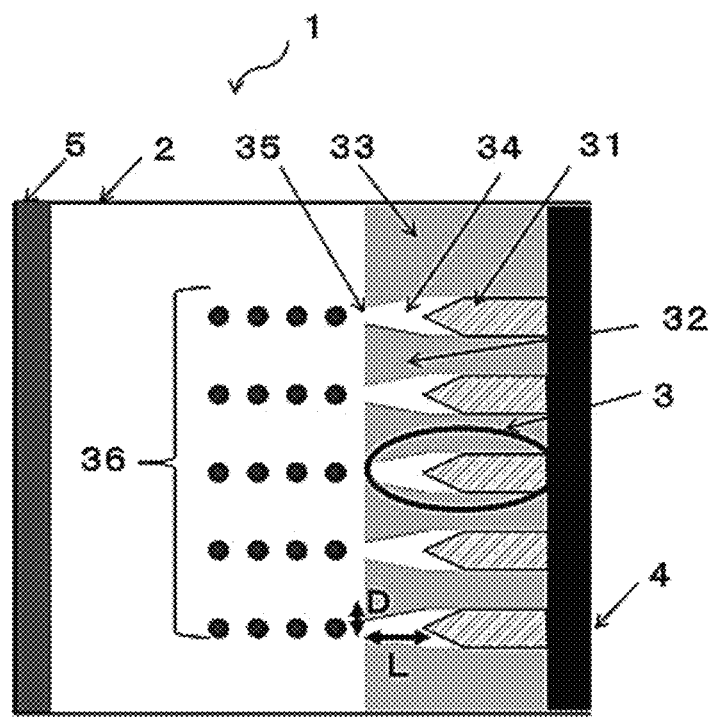
FIG. 1 illustrates a scheme of the bubble-jetting chip 1 of the present invention.

FIG. 1 illustrates a scheme of the bubble-jetting chip 1 of the present invention. The bubble-jetting chip 1 of the present invention has a bubble-jetting portion 3 formed on a substrate 2. The bubble-jetting portion 3 has an electrode 31 that is formed of a conductive material, an insulating portion 33 that is provided so as to sandwich the electrode and includes an extended section 32 that extends beyond the tip of the electrode 31, and a space 34 that is formed between the tip of the electrode 31 and the extended section 32. Also, in the example illustrated in FIG. 1, there is formed an energizing portion 4 that connects to the electrode 31, but the energizing portion 4 may be formed integrally when producing the bubble-jetting chip 1, or may be produced separately from the bubble-jetting chip 1 and be connected upon energizing. Also, a counter electrode 5 is formed on the substrate 2, but the counter electrode 5 may be formed integrally when producing the bubble-jetting chip 1, or may be produced separately from the bubble-jetting chip 1 and be immersed in a solution when energizing. Bubbles 36 can be continuously jetted from a bubble-jetting outlet 35 formed by adjacent extended sections 32, by applying voltage to the electrode 31 and the counter electrode 5.

The material for forming the substrate 2 is not particularly limited provided that the electrode 31 and insulating portion 33 can be deposited thereon. Examples include glass, quartz, PMMA, and silicon.

The material for forming the electrode 31 is not particularly limited provided that the material can be energized and can be layered on the substrate 2 by electroplating, electroless plating, or other methods. Examples include nickel, gold, platinum, silver, copper, tin, magnesium, chromium, tungsten, and other metals, or alloys thereof.

In the present invention, the insulating portion 33 including the extended section 32 is made by using photolithography. Accordingly, the material for forming the insulating portion 33 including the extended section 32 is not particularly limited provided that the material is an insulating photosensitive resin. Examples include commercial TSMR V50, PMER, and other positive photoresists, and SU-8, KMPR, and other negative photoresists. In the present invention, because bubbles 36 are jetted by energizing the electrode 31 and the counter electrode 5, a load is easily applied to the bubble-jetting outlet 35, which is a very small portion, particularly when high voltage is applied thereto. Because SU-8, KMPR, and other negative photoresists have higher hardness than positive photoresists, a negative photoresist is preferably used as the photosensitive resin when high voltage is applied to the bubble-jetting portion 3.

The material of the energizing portion 4 and the counter electrode 5 is not particularly limited provided that electricity can be delivered from an external power supply to the electrode 31, and the same material as that of the above-mentioned electrode 31 can be used. When the energizing portion 4 is produced separately from the bubble-jetting chip 1, the end of the electrode 31 should extend from the insulating portion 33, and the energizing portion 4 should be produced so as to be easily connected. Also, when the counter electrode 5 is produced separately, the counter electrode 5 should be capable of being energized with the electrode 31 and therefore is not particularly limited to being in the form of a rod, sheet, or other shape.

Because bubbles formed in the space 34 are jetted from the bubble-jetting outlet 35 so as to be torn off when electricity is outputted to the electrode 31 and the counter electrode 5, there is no need to supply air from the outside to the bubble-jetting portion 3. Also, the space 34 preferably becomes smaller nearer to the bubble-jetting outlet 35 in order to provide the jetted bubbles 36 with directionality, and in the manufacturing steps to be discussed below, a photomask that is shaped so that the extended section 32 is tapered should be used.

Also, when bubbles are formed inside the space 34, bubbles having a size near the inner diameter (indicated as "diameter D" or "D" below) of the bubble-jetting outlet 35 are produced. Accordingly, the depth (length from the tip of the electrode 31 to the bubble-jetting outlet 35; indicated as "L" below) of the space 34 must be large enough for bubbles to be produced inside the space 34, and the L/D ratio is preferably at least 1. Meanwhile, the upper limit of the L/D ratio is not particularly limited provided that the size is sufficient for bubbles to be continuously jetted. Because the bubble-jetting member described in Patent Document 1 is produced by heating and pulling apart, etc., the tip of the bubble-jetting member is very sharp and easily damaged, but in the case of the present invention, the bubble-jetting outlet is formed of a photosensitive resin on a substrate, which eliminates the risk of damage. The L/D ratio can be adjusted according to the shape of the photomask. The size of the jetted bubbles 36 can be adjusted by changing the diameter D of the bubble-jetting outlet 35, and should be adjusted by the shape of the photomask during production.

Figure 2:
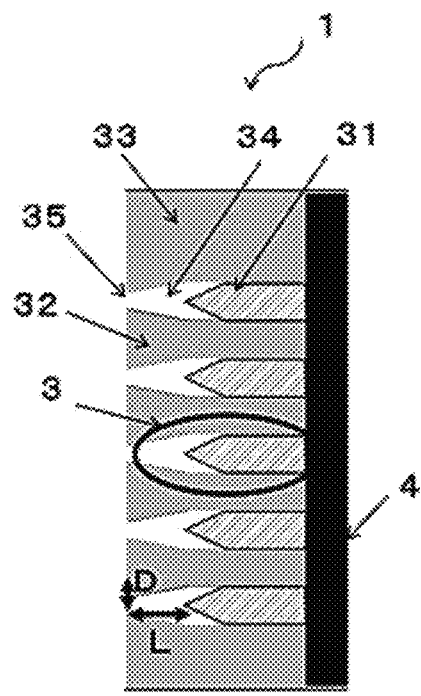
FIG. 2 illustrates another embodiment of the bubble-jetting chip 1.

FIG. 2 illustrates another embodiment of the bubble-jetting chip 1. When the counter electrode 5 is produced separately, the size of the substrate 2 should be the same size as that of the bubble-jetting portion 3 (insulating portion 33). In the case of the embodiment illustrated in FIG. 1, the bubble-jetting chip 1 must be immersed in a solution through which electricity can be passed, or the solution must be poured on the substrate 2 so that the counter electrode has continuity with the electrode, and the process target must be arranged on the substrate 2, but with the bubble-jetting chip 1 illustrated in FIG. 2, at least the bubble-jetting outlet 35 should be immersed in the solution. Regardless of the form, the solution should be poured so that the counter electrode has continuity with the electrode during use.

Although not illustrated in FIG. 1 and FIG. 2, it is desirable to form an insulating layer on the top surface when using the bubble-jetting chip 1 in order to prevent leakage of electricity when the bubble-jetting chip 1 is immersed in the solution. The material used for forming the insulating material should be polydimethylsiloxane (PDMS), parylene, epoxy resin, polyimide, polyethylene, glass, quartz, PMMA, silicon, or other well-known insulating material. The insulating layer may be affixed to the bubble-jetting chip 1 before use, or may be formed in advance during manufacture of the bubble-jetting chip 1.

Figures 1, 3:
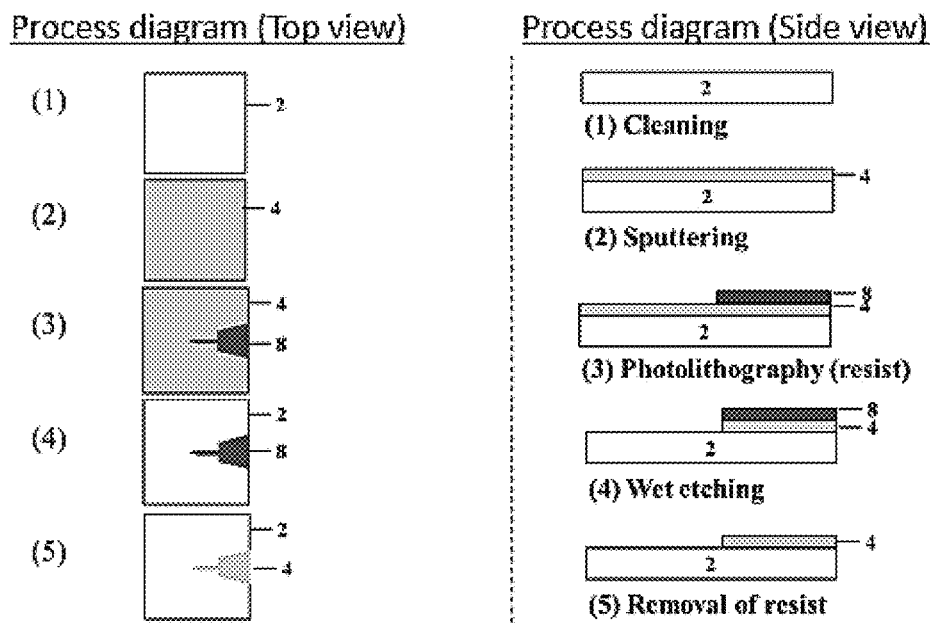
FIG. 3 illustrates one example of the manufacturing steps in a first embodiment of the bubble-jetting chip 1 of the present invention.
Figures 2, 3:
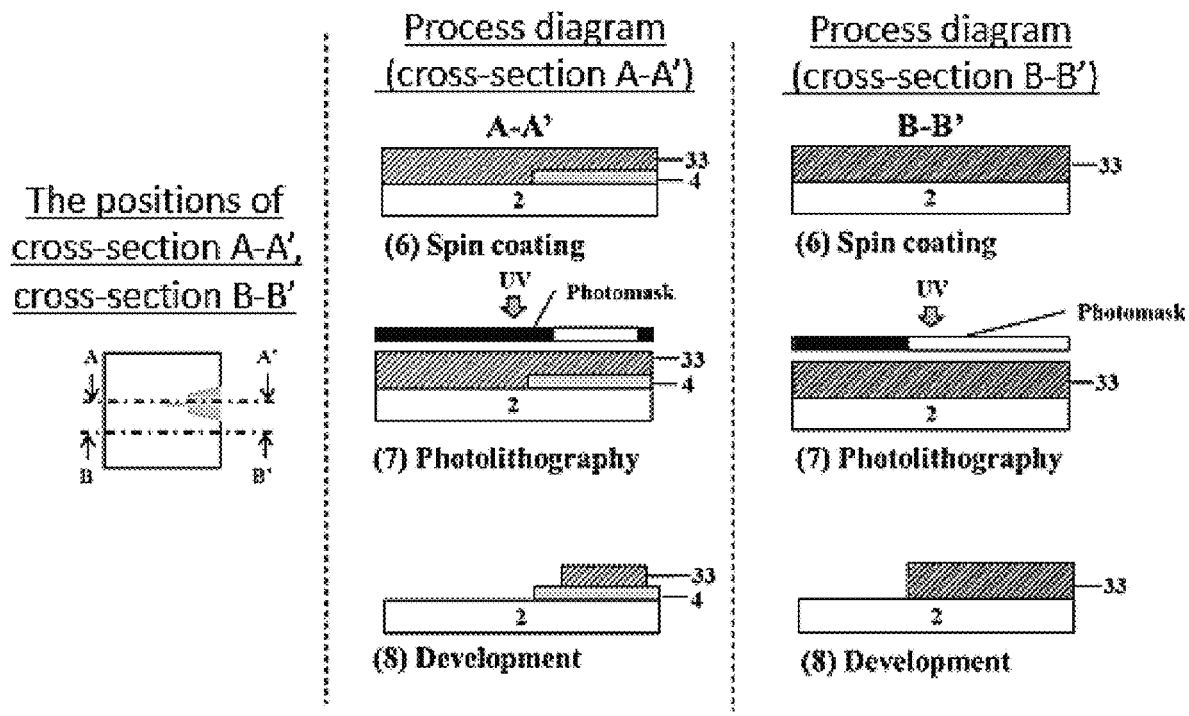
Figure 3:
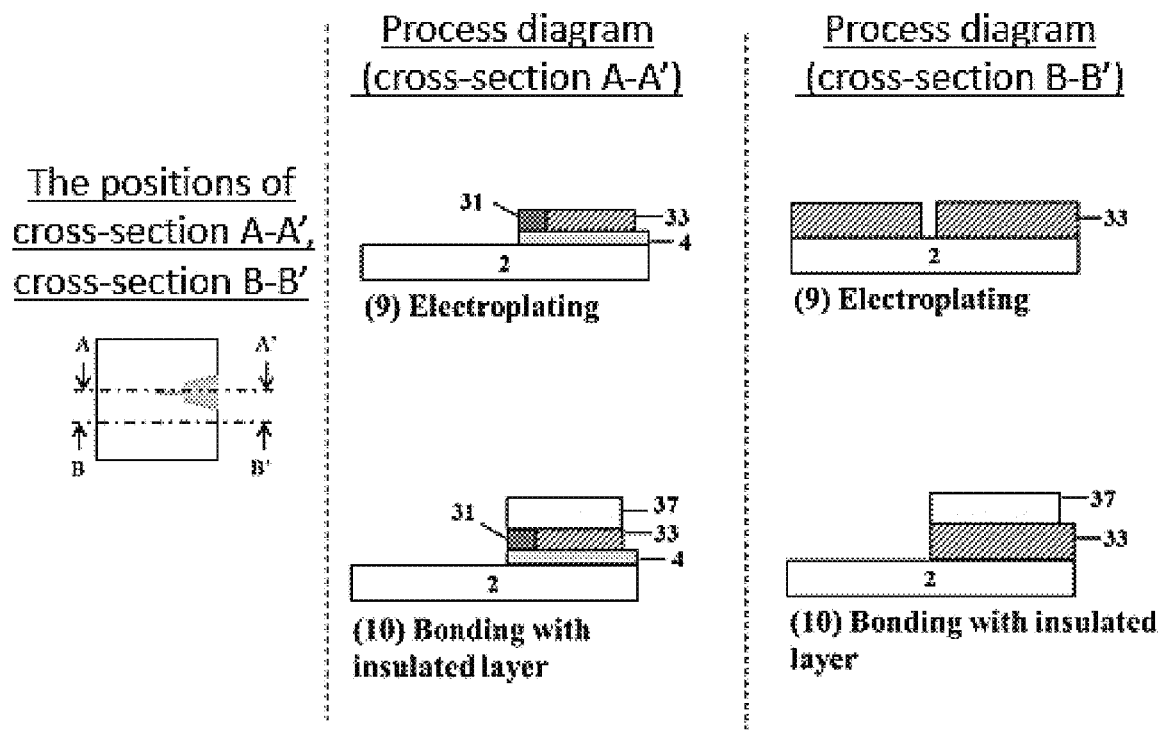

FIG. 3 illustrates one example of the manufacturing steps in a first embodiment of the bubble-jetting chip 1 of the present invention. In FIG. 3, an example in which there is one bubble-jetting portion 3 is shown in regard to the depicted relationship, but the shape of the photomask may be changed when a plurality of bubble-jetting portions 3 is formed.

(1) The substrate 2 is cleaned with acetone, ethanol, ultrapure water, etc.

(2) The material for forming the energizing portion 4 is layered on the substrate 2 by sputtering.

(3) A photoresist 8 is applied, and photoexposure and development are performed using a mask so that the photoresist 8 remains in the portion where the energizing portion 4 is ultimately to be formed.

(4) The material other than the portion where the energizing portion 4 is to be formed is removed by wet etching or another method.

(5) The photoresist 8 is removed, whereby the energizing portion 4 is formed. As for the manufacturing steps below, the portion where the electrode 31 is formed is illustrated as cross-section A-A', and the portion where the insulating portion 33 including the extended section 32 (only the reference symbol 33 is indicated on the drawing) is formed is illustrated as cross-section B-B'. The positions of cross-section A-A' and cross-section B-B' are illustrated in the drawing for (5) above (left side of FIG. 3-2 and FIG. 3-3).

(6) The material for forming the insulating portion 33 including the extended section 32 is layered by spin coating.

(7) Photoexposure is performed using a photomask designed to a shape such that the insulating portion 33 including the extended section 32 remains. In order to facilitate connection to an external power supply, it is desirable to use a photomask having a shape such that the insulating portion 33 on the end portion of the substrate 2 is removed and the energizing portion 4 is exposed.

(8) After development, the material other than the portion where the insulating portion 33 including the extended section 32 is formed is removed.

(9) An electrode 31 is grown by electroplating on the energizing portion 4. (10) An insulating layer 37 is formed.

The resists, etchants, sputtering devices, etc., used in the abovementioned steps may be publicly known reagents and devices used in the field of micromachining technology.

In the abovementioned manufacturing steps, the electrode 31 was grown by electroplating on the energizing portion 4, but an energizing portion 4 need not be provided. Specifically, an insulating portion 33 should be formed on a substrate 2 by omitting steps (2) to (4), and next a material for forming a thin-plate-form electrode 31 should be cut to the shape of the electrode 31 and be sandwiched inside the insulating portion 33. In that case, the electrode 31 is preferably formed so as to be exposed on the end of the substrate 2, and is preferably arranged to be capable of being energized directly by an external power supply. Also, in the abovementioned manufacturing steps, an example was illustrated in which the bubble-jetting portion 3 was arranged two-dimensionally on the substrate 2, but the bubble-jetting portion 3 can be formed three-dimensionally on the substrate 2 by repeating steps (2) to (10) after completing step (10).

Figure 4:
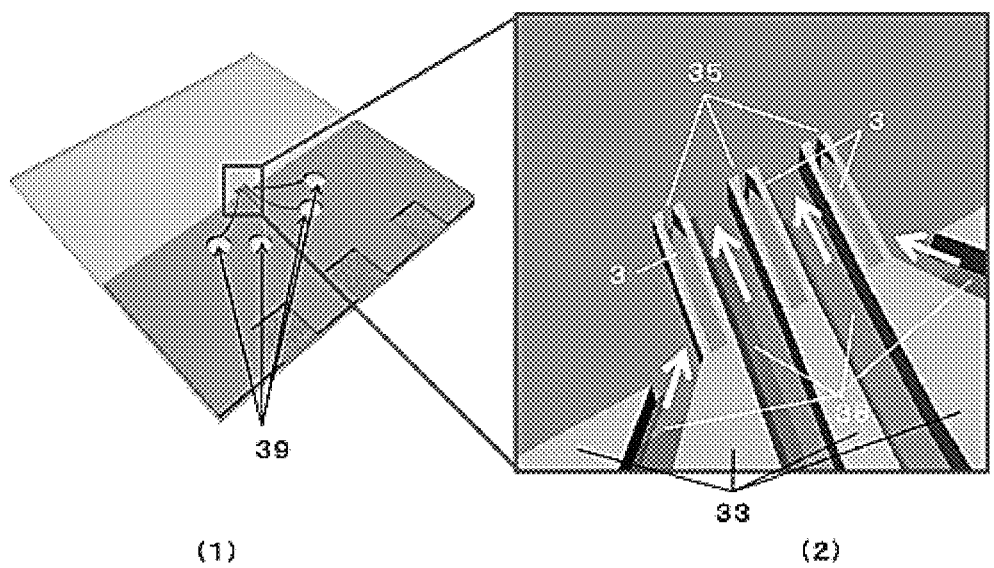
FIG. 4 illustrates another embodiment of the bubble-jetting chip 1 of the present invention.

FIG. 4 is an illustration of another embodiment of the bubble-jetting chip 1 of the present invention; FIG. 4(1) is the entirety of the bubble-jetting chip 1, and FIG. 4(2) is an enlarged view in the vicinity of the bubble-jetting portion 3. As mentioned above, the bubble-jetting chip 1 of the present invention may have an insulating layer 37 formed on the top surface of the bubble-jetting chip 1 in order to prevent leakage of electricity. In this case, if the distance between the bubble-jetting outlet 35 and the process target is long, the bubbles 36 jetted from the bubble-jetting outlet 35 may move forward through the solution, but the bubbles 36 might also move to the side of the insulating layer 37 due to buoyancy and attach to the insulating layer 37. Therefore, an assist channel 38 may be formed on the insulating portion 33 to form an assist flow (arrow in FIG. 4(2)) to push the jetted bubbles 36 out forward.

The assist channel 38 is not particularly limited provided that an assist flow to push the bubbles 36 out forward can be formed as mentioned above. For example, the assist flow should be formed so as to flow along the bubble-jetting portion 3. In the example illustrated in FIG. 4(2), assist channels 38 are provided on both ends of a plurality of bubble-jetting portions 3 and between respective bubble-jetting portions 3, but an assist channel 38 may be formed for each of a plurality of bubble-jetting portions 3. Also, in the example illustrated in FIG. 4(2), the bubble-jetting portions 3 project from the insulating portion 33, but an assist channel 38 may be formed on a bubble-jetting chip 1 having a shape in which the bubble-jetting portions 3 do not project from the insulating portion 33 illustrated in FIG. 1 and FIG. 2. The assist channel 38 should be formed on the insulating portion 33 by changing the shape of the photomask in manufacturing step (7). Also, when forming the assist channels 38, pump connection parts 39 for connecting a pump to send liquid into the assist channels 38 may be formed on the ends of the assist channels 38 as illustrated in FIG. 4(1). The pump connection parts 39 also should be formed on the insulating portion 33 by changing the shape of the photomask in manufacturing step (7). When forming the pump connection parts 39, a hole should be formed in the insulating layer 37 on the top surface of the bubble-jetting chip 1, and a silicon tube, etc., should be connected to the hole.

Figure 5:
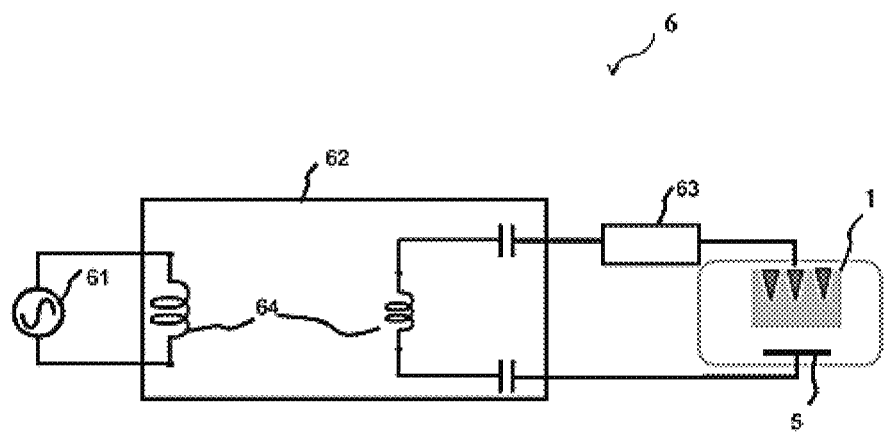
FIG. 5 illustrates the overall configuration of a localized ablation device 6 using the bubble-jetting chip 1 of the present invention.

FIG. 5 illustrates the overall configuration of a localized ablation device 6 using the bubble-jetting chip 1 of the present invention. The localized ablation device 6 includes electricity output device. The electricity output device includes at least a generic commercial AC power supply device 61, and an electric wire 62 for forming a circuit between the electrode 31 of the bubble-jetting chip 1 and the counter electrode 5, and may also have a non-dielectric resistor 63, a voltage amplification circuit 64, a digital input/output (DIO; not shown) port, etc., as needed. The electricity output device can be fabricated merely by incorporating a non-dielectric resistor 63, DIO port, etc. in a conventional electrical circuit for an electric scalpel, and setting to an output configuration for use on microscopic objects.

The current, voltage, and frequency of output to the electrode 31 and the counter electrode 5 are not particularly limited provided that the ranges are such that bubbles can be jetted and the bubble-jetting portion 3 is not damaged. For example, the current is preferably 10 mA to 80 mA, and more preferably 25 mA to 75 mA. It is undesirable for the current to be less than 10 mA, since it may not be possible to properly produce bubbles 36, or for the current to be greater than 80 mA, since wear of the electrode may occur. The voltage is preferably 100 V to 800 V, and more preferably 200 V to 600 V. It is undesirable for the voltage to be smaller than 100 V, since generation of bubbles 36 may be difficult, or for the voltage to be greater than 800 V, since wear of the electrode 31 or damage to the extended section 32 might occur. The frequency is preferably 1 kHz to 1 GHz, more preferably 5 kHz to 1 MHz, and particularly preferably 10 kHz to 60 kHz. It is undesirable for the frequency to be less than 1 kHz, since the extended section 32 might be damaged, or for the frequency to be greater than 1 GHz, since it might not be possible to produce bubbles 36.

In the localized ablation method of the present invention, first, the bubble-jetting chip 1 of the localized ablation device 6 of the present invention and the counter electrode 5 are immersed in a conductive solution, or the solution is poured on the substrate 2 so that the counter electrode 5 conducts with the electrode 31. A process target is arranged between the bubble-jetting portion 3 of the bubble-jetting chip 1 and the counter electrode 5, bubbles 36 jetted from the bubble-jetting portion 3 are cause to collide with the process target, whereby localized ablation of the process target can be performed.

The process target is not particularly limited provided that ablation can be performed thereon using bubbles. Examples include cells and proteins. Examples of cells include stem cells isolated from human or non-human animal tissues, skin cells, mucous cells, liver cells, islet cells, nerve cells, cartilage cells, endothelial cells, epithelial cells, bone cells, muscle cells, egg cells, and other animal cells, and plant cells, insect cells, *E. coli*, yeast, molds, and other microbial cells, and other cells. "Processing" in the present invention signifies jetting bubbles on a process target to open holes in the target or cut a portion of the target.

In Patent Document 1, the present inventors demonstrated that bubbles jetted from the bubble-jetting member could adsorb an injection material. Presumably, the bubbles produced by energizing the core are charged with electricity and the injection material is adsorbed onto the bubbles due to the electricity. Accordingly, when performing localized ablation using the bubble-jetting chip 1 illustrated in FIG. 1 or FIG. 2, if an injection material is caused to be contained in the conductive solution in which the bubble-jetting chip 1 is immersed, bubbles 36 around which the injection material is adsorbed can be jetted. Therefore, the injection material can be introduced while performing localized ablation on the process target. The height from the substrate 2 to the insulating layer 37 of the bubble-jetting chip 1 of the present invention is on the micron order. Accordingly, in terms of fluid mechanics, a laminar flow of a solution containing an injection material can be formed by using a pump, etc., to push out a solution containing the injection material into a conductive solution.

Figure 6:
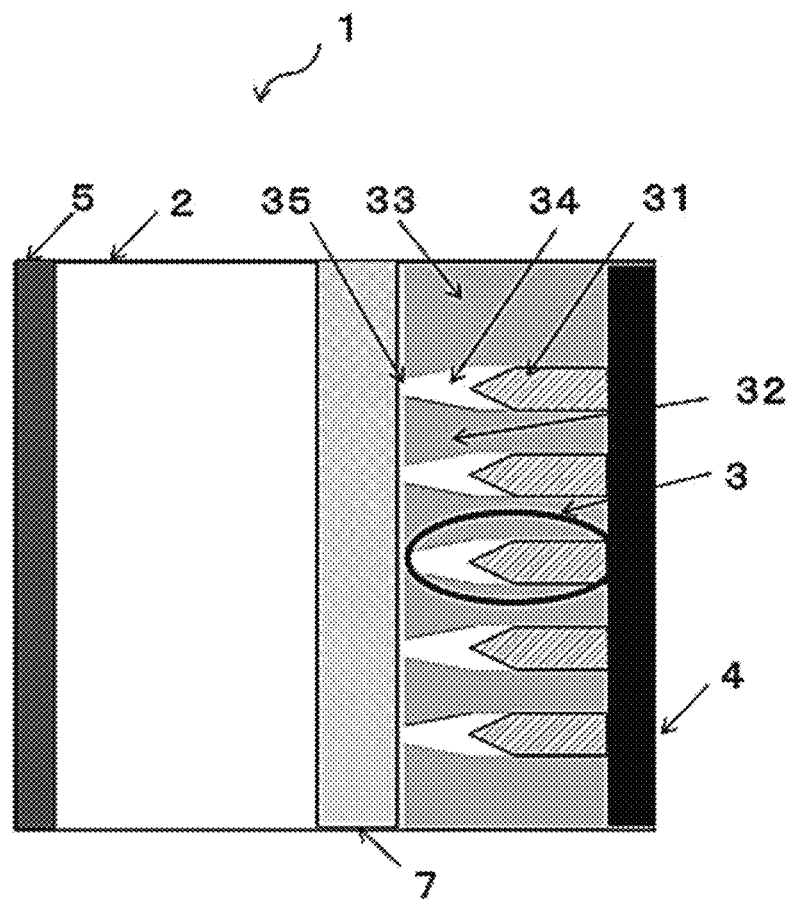
FIG. 6 illustrates a scheme of the bubble-jetting chip 1 applied to an injection device.

FIG. 6 illustrates a scheme of the bubble jetting chip 1 (referred to below as "bubble-jetting chip for injection") applied to an injection device. The bubble-jetting chip 1 for injection illustrated in FIG. 6 has a channel 7 for delivering a solution containing an injection material (referred to below as "injection solution channel") formed on the space 34 side of the bubble-jetting portion 3. Although, in terms of fluid mechanics, the solution containing the injection material can be rendered into a laminar flow as mentioned above even without forming an injection solution channel 7 in particular, forming an injection solution channel 7 facilitates the solution containing the injection material forming a laminar flow. FIG. 7(1-1) is a cross-sectional view of one example of the bubble-jetting chip 1 for injection, and FIG. 7(1-2) is a top view of the same. In the example illustrated in FIGS. 7(1-1) and (1-2), by not forming the energizing portion 4 in the portion corresponding to the injection solution channel 7, a channel 7 is formed by making that portion relatively lower than the remaining portion.

FIG. 7(2-1) is a cross-sectional view of another example of the bubble-jetting chip 1 for injection, and FIG. 7(2-2) is a top view of the same. In the example illustrated in FIGS. 7(2-1) and (2-2), by forming an insulating wall 71 on the opposite side from the bubble-jetting portion 3, a channel 7 is formed by the extended section 32 of the bubble-jetting portion 3 and the insulating wall 71. In the case of the bubble-jetting chip 1 for injection illustrated in FIGS. 7(2-1) and (2-2), the bubbles 36 pass through the channel 7, whereby bubbles 36 around which the injection material is adsorbed can be formed. Therefore, because the process target must be away from the channel 7, it is desirable to form a process-target-placement channel 72 for placement of the process target on the insulating wall 71 facing the bubble-jetting portion 3. The same material as that for the insulating portion 32 should be used for the insulating wall 71. In the example illustrated in FIGS. 7(2-1) and (2-2), if the channel 7 is very narrow and only the solution containing the injection material is to be delivered, then the process-target-placement channel 72 must be formed and the conductive solution must be filled inside the process-target-placement channel 72. Meanwhile, if the channel 7 is wide and a laminar flow of the solution containing the injection material can be formed inside the conductive solution inside the channel 7, then the process target can be arranged inside the channel 7 and there is no need for a process-target-placement channel 72.

Although not illustrated in FIG. 7, an injection port for delivering an injection material into the channel 7 is formed on the bubble-jetting chip 1 for injection. By injecting from the injection port a solution containing an injection material that is adjusted so that the degree of hydrophilicity differs from that of the conductive solution, a solution flow containing the injection material can be formed in the conductive solution in which the bubble-jetting chip 1 is immersed.

Also, the injection port is not limited to one; a plurality thereof may be formed. By injecting from the respective injection ports injection materials that are adjusted to have different degrees of hydrophilicity, a multilayer solution flow containing the injection materials can be formed. When forming the injection port, a discharge port should be formed on the opposite side from the channel 7. The injection port and the discharge port should be formed as holes in the insulating layer 37 on the top surface of the bubble-jetting chip 1, and silicon tubes, etc., should be connected to the holes.

Figures 2, 8:
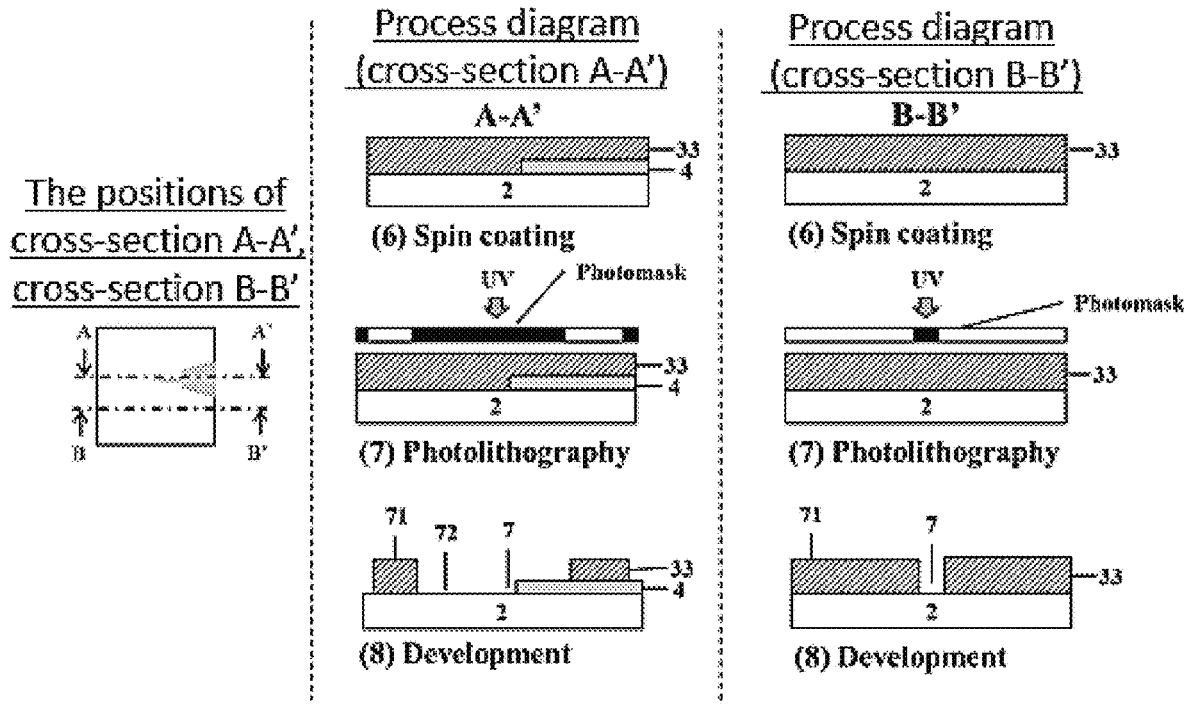
FIG. 8 illustrates one example of a step for manufacturing the bubble-jetting chips 1 for injection illustrated in FIGS. 7(2-1) and (2-2)
Figures 3, 8:
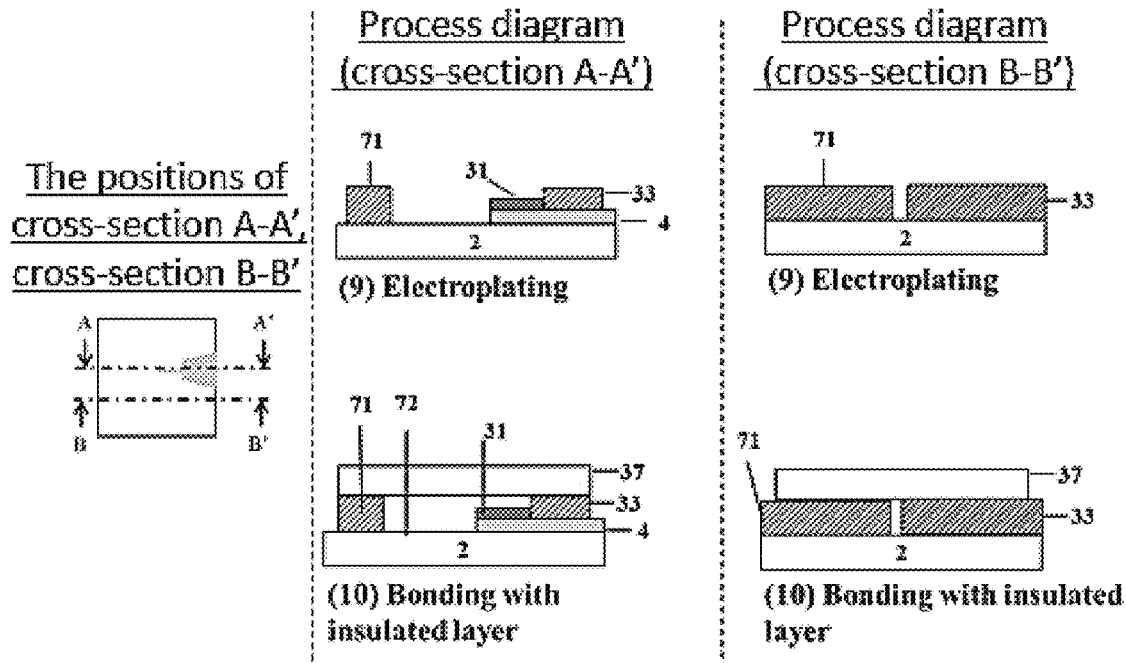
Figure 9:
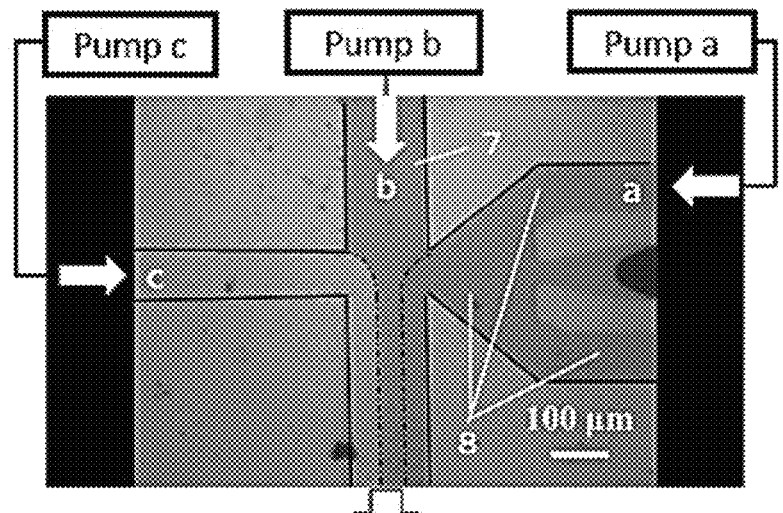
FIGS. 9(1) and (2) illustrate other embodiments of the bubble-jetting chip 1 for injection.
Figure 9:
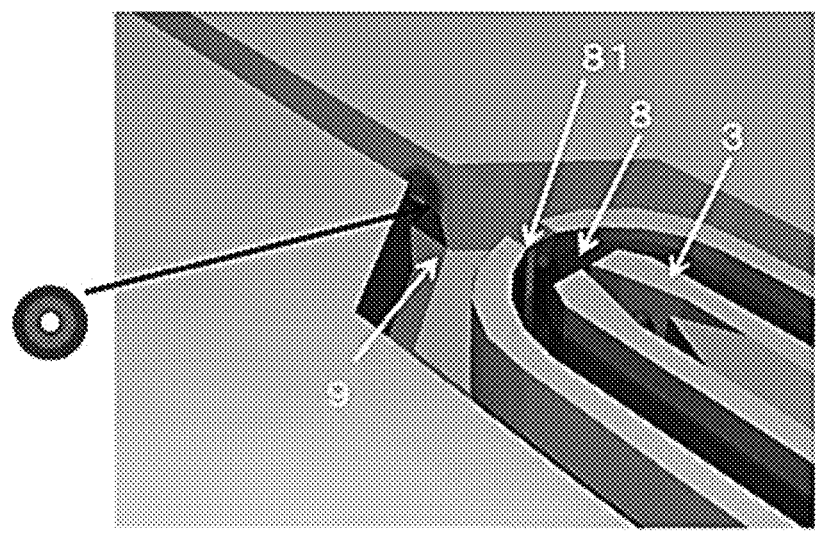

FIG. 8 illustrates one example of the process for production of the bubble-jetting chips 1 for injection illustrated in FIGS. 7(2-1) and (2-2). The manufacturing steps are the same as those illustrated in FIG. 3, except that in step (7) of the steps illustrated in FIG. 3, the photomask is formed as a shape that can produce an insulating layer 71 and an process-target-placement channel 72. FIG. 9 illustrates another embodiment of the bubble-jetting chip 1 for injection. In the bubble-jetting chip 1 for injection illustrated in FIGS. 6 and 7, the bubble-jetting outlet 35 faces the injection solution channel 7, but in the bubble-jetting chip 1 for injection illustrated in FIG. 9(1), a first injection solution channel 8 containing a first injection material is formed around the bubble-jetting portion 3, and the first injection solution channel 8 is connected to the injection solution channel 7 illustrated in FIG. 6 and FIG. 7. In the embodiment illustrated in FIG. 9(1), an injection flow a containing injection material from a pump a is formed in the first injection solution channel 8, an injection b containing injection material from pump b is formed in the injection solution channel 7, and the injection flows a and b assume a laminar flow. In this case, the injection flow a serves the function of the assist flow previously discussed. The first injection material contained in the solution flowing in the first injection solution channel 8 is adsorbed around the bubbles jetted from the bubble-jetting outlet, and the injection material contained in the solution flowing in the injection solution channel 7 is adsorbed therearound. By placing the process target near the entrance of the process-target-placement channel 72 and increasing the voltage applied to the bubble-jetting portion 3, a pump c for forming an injection flow c containing an injection material can be placed also in the process-target-placement channel 72, and the injection flow can be formed into three layers.

Also, in the embodiment illustrated in FIG. 9(2), a first injection solution channel 8 containing a first injection material is formed around the bubble-jetting portion 3, and a hole 81 for allowing the passage of bubbles onto which the first injection material was adsorbed is formed in the first injection solution channel 8. Furthermore, a second injection solution channel 9 containing a second injection material is formed around the first injection solution channel 8. In the embodiment illustrated in FIG. 9(2), the first injection material flowing in the first injection solution channel 8 can be adsorbed around the bubbles jetted from the bubble-jetting outlet, and the second injection material flowing in the second injection solution channel 9 can be adsorbed around that.

Although not illustrated in FIG. 9(2), pump connection parts for connecting the pumps for pumping the solutions containing the injection materials may be formed on the ends of both injection solution channels 8, 9. The injection solution channels 8, 9 and the pump connection parts should be formed on the insulating portion 33 by changing the shape of the photomask in manufacturing step (7) mentioned above. When forming the pump connection parts, holes should be formed in the insulating layer 37 on the top surface of the bubble-jetting chip 1 for injection, and silicon tubes, etc., should be connected to the holes.

An injection device can be produced by using the bubble-jetting chip 1 for injection instead of the bubble-jetting chip 1 of the localized ablation device 6 mentioned above. Except for delivering a solution containing an injection material in the channel 7, the same procedure as the localized ablation method can be used to introduce the injection material while performing localized ablation on a process target. As shall be apparent, if a conductive solution not containing an injection material is used, then use as a localized ablation device also is possible.

The injection material is not particularly limited, whether gas, solid, or liquid, provided that the material can be dissolved and/or dispersed in a liquid. Examples of gases include air, nitrogen, helium, carbon dioxide, carbon monoxide, argon, and oxygen; examples of solids include DNA, RNA, proteins, amino acids, and inorganic substances; and examples of liquids include chemical solutions and amino acid solutions. Examples of solutions for dissolving and/or dispersing the injection materials include physiological saline and culture media.

The present invention is described specifically below with examples, but these examples are provided simply for reference to specific embodiments for description of the present invention. Although these illustrations are for describing specific embodiments of the present invention, they do not represent restrictions or limitations on the scope of the present invention disclosed in the present application.

EXAMPLES

Example 1

[Production of Bubble-Jetting Chip 1]

(1) A glass substrate was organically cleaned with an ultrasonic cleaner at 100 kHz for 5 minutes each with acetone, ethanol, and ultrapure water in the stated order, and was baked at 120° C. for 30 minutes.

(2) The glass substrate was cooled to normal temperature, and Au was then formed into a film on the glass substrate using a sputtering device (Vacuum Device MSP-30T) with plasma current value (80 mA) for one minute.

(3) OFPR-800LB (200 CP) was spun-coated on the glass substrate at 2000 rpm for 30 seconds and 4000 rpm for 2 seconds, and the coated substrate was pre-baked in an oven at 90° C. for 30 minutes. Next, photoexposure was performed using an emulsion mask, and development was performed using NMD-3. After development, the resulting product was rinsed with ultrapure water and dried upon the water being cast off in a spin dryer, etc.

(4) The areas other than the patterned OFPR were soaked with an Au etchant (AURUM-302, Kanto Chemical) to etch the Au, and the resulting product was rinsed with ultrapure water.

(5) The glass substrate was immersed in acetone and the remaining OFPR film was removed, with which patterning of the Au electrode portion concluded.

(6) SU-8 was spun-coated on the glass substrate, and the coated substrate was pre-baked on a hot plate at 95° C. for 50 minutes.

(7) Photoexposure was performed using an emulsion mask, and then the resulting product was post-exposure baked on a hot plate at 95° C. for 5 minutes.

(8) Development was performed using PGMEA (2-Methoxy-1-methylethyl acetate; CAS Number: 142300-

82-1). After development, the resulting product was rinsed with ultrapure water and dried, with the water being cast off in a spin dryer, etc., with which the SU-8 patterning operation concluded.

(9) An electrode was connected to the Au patterned part, and Ni plating was grown to the height (100 µm) of the SU-8 pattern along the SU-8 patterning, resulting in a bubble-jetting chip 1.

(10) Polydimethylsiloxane (PDMS) was spun-coated on an OHP film at 1000 rpm for 20 seconds, and the resulting product was baked at 90° C. for 15 minutes to prepare a sheet having a thickness of about 100 µm. The PDMS sheet was placed covering the top surface of the produced bubble-jetting chip 1, and bonded thereto using an adhesive agent (Super X, Cemedine).

Figure 10:
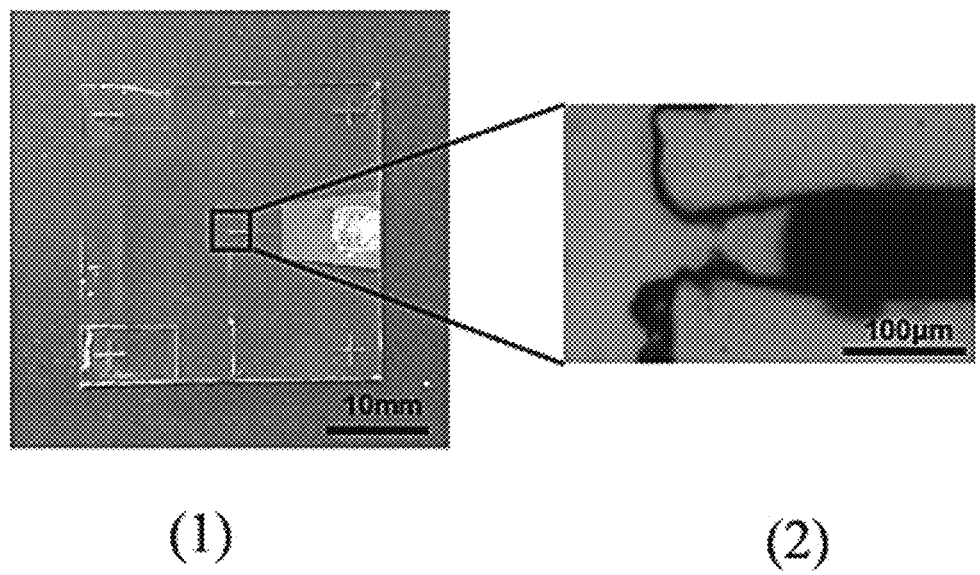
FIG. 10 is a photograph substituting for a drawing.

FIG. 10(1) is a photograph of the bubble-jetting chip 1 produced in example 1, and FIG. 10(2) is a photograph enlarging the vicinity of the bubble-jetting portion. The bubble-jetting outlet 35 was about 50 ||m in size.

Example 2

[Production of Bubble-Jetting Chip 1]

Figure 11:
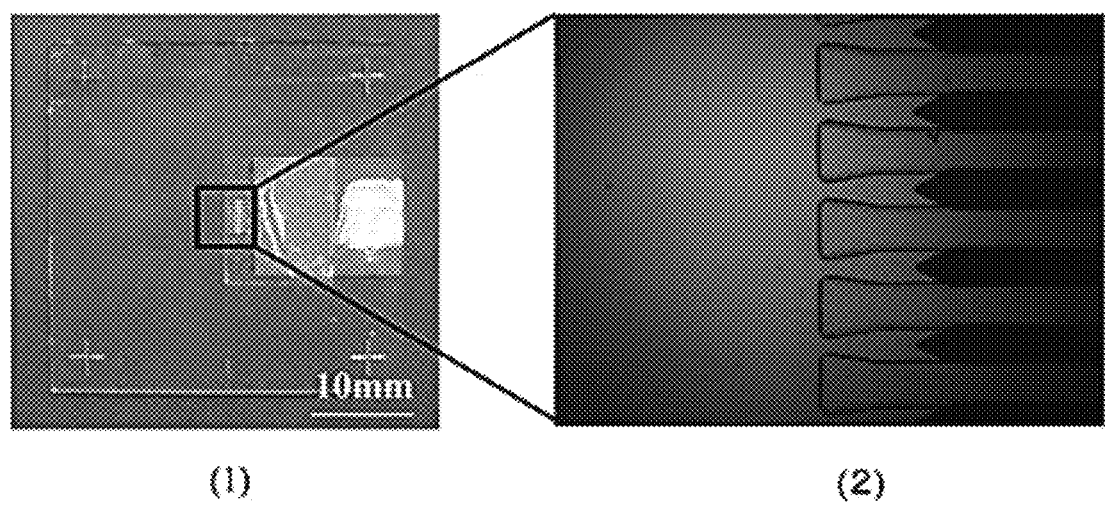
FIG. 11 is a photograph substituting for a drawing.

The shape of the emulsion mask in step (7) of the abovementioned example 1 was changed, and a bubble-jetting chip 1 having a plurality of bubble jetting portions formed was fabricated. FIG. 11(1) is a photograph of the bubble-jetting chip 1 produced in example 2, and FIG. 11(2) is a photograph showing an enlargement of the vicinity of the bubble-jetting portion. The bubble-jetting outlet 35 was about 50 µm in size.

Example 3

[Production of Localized Ablation Device and Injection Device and Bubble Jetting Experiment]

The bubble-jetting chip 1 produced in example 1 was incorporated in place of the scalpel of an electric scalpel for medical use (product of ConMed Corp., Hyfrecator 2000), a non-dielectric resistor and a DIO port were furthermore incorporated in the electricity output device, and a localized ablation device and injection device were thus produced.

Next, the bubble-jetting chip 1 was immersed in a 5M NaCl solution, and electricity was outputted to the electrode 31 and the counter electrode 5 with a voltage of 27.7 mA, a current of 309 V, an output frequency of 450 kHz, a sampling frequency for impedance matching of 450 kHz, and feedback at 3.5 kHz. The formation of bubbles was captured using a high-speed camera (VW-9000, product of Keyence Corp.). The counter electrode 5 was produced with a copper plate, and was away from the bubble-jetting chip 1.

Figure 12:
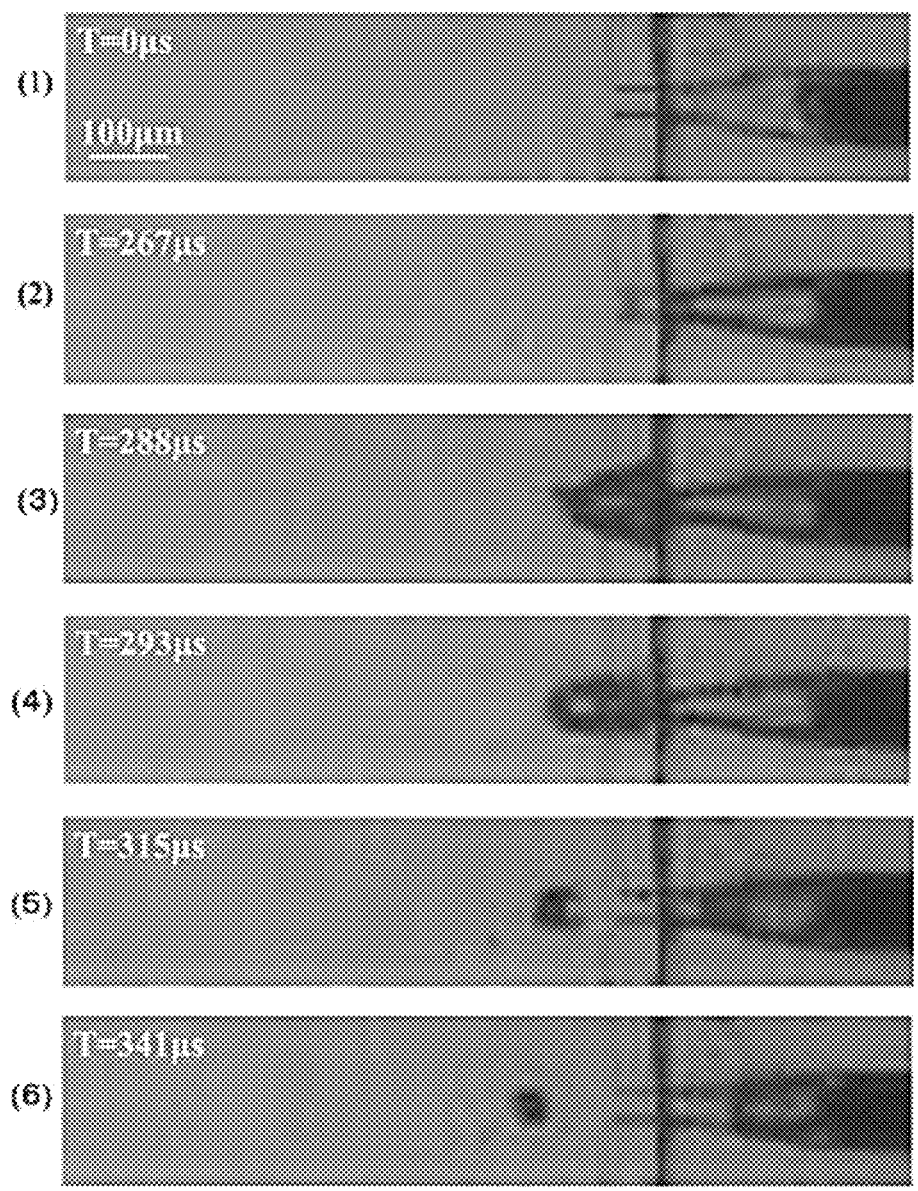
FIG. 12 is a photograph substituting for a drawing, and is a photograph of the generation of bubbles 36 captured with a high-speed camera in example 3.

FIG. 12 is a photograph of the generation of bubbles 36 captured by a high-speed camera. As is clear from the photograph, it was confirmed that bubbles 36 could be jetted from the bubble-jetting outlet 35 by using the bubble-jetting chip 1 produced in example 1.

Example 4

Figure 13:
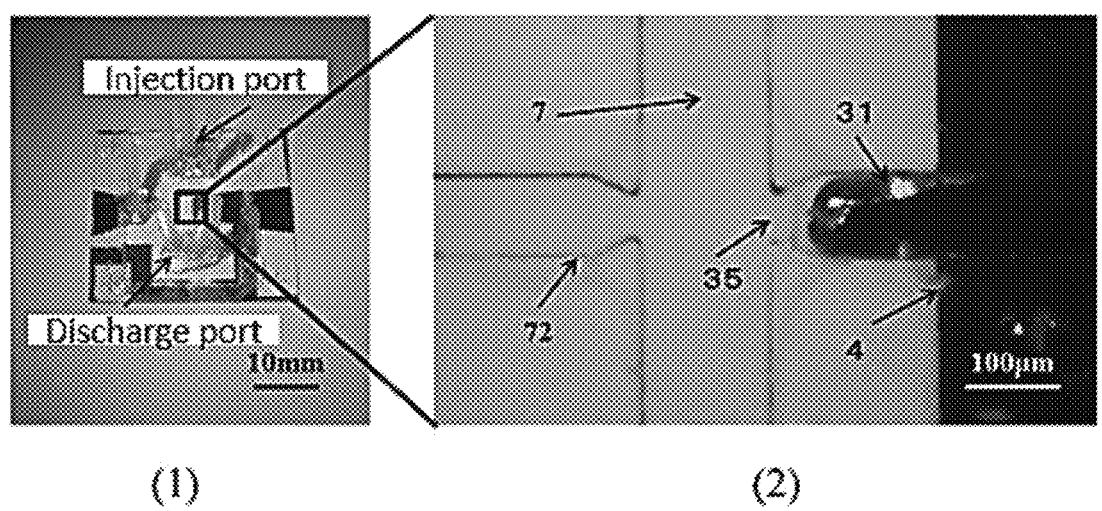
FIG. 13 is a photograph substituting for a drawing.

A bubble-jetting chip 1 including a channel 7 was produced by changing the shape of the emulsion mask in step (7) of the abovementioned example 1. FIG. 13(1) is a photograph of the bubble-jetting chip 1 produced in example 4, and FIG. 13(2) is a photograph showing an enlargement of the vicinity of the bubble-jetting portion. The bubble-jetting outlet 35 was 50 µm in size, the electrode 31 was 25 µm in height, the channel 7 was 50 µm in height, and the width was 100 µm.

[Production of Localized Ablation Device and Injection Device and Bubble Jetting Experiment]

Example 5

A localized ablation device and an injection device were produced using the same device as in example 3, except that the bubble-jetting chip 1 produced in example 4 was used instead of the bubble-jetting chip 1 produced in example 1, and a bubble jetting experiment was performed.

Figure 14:
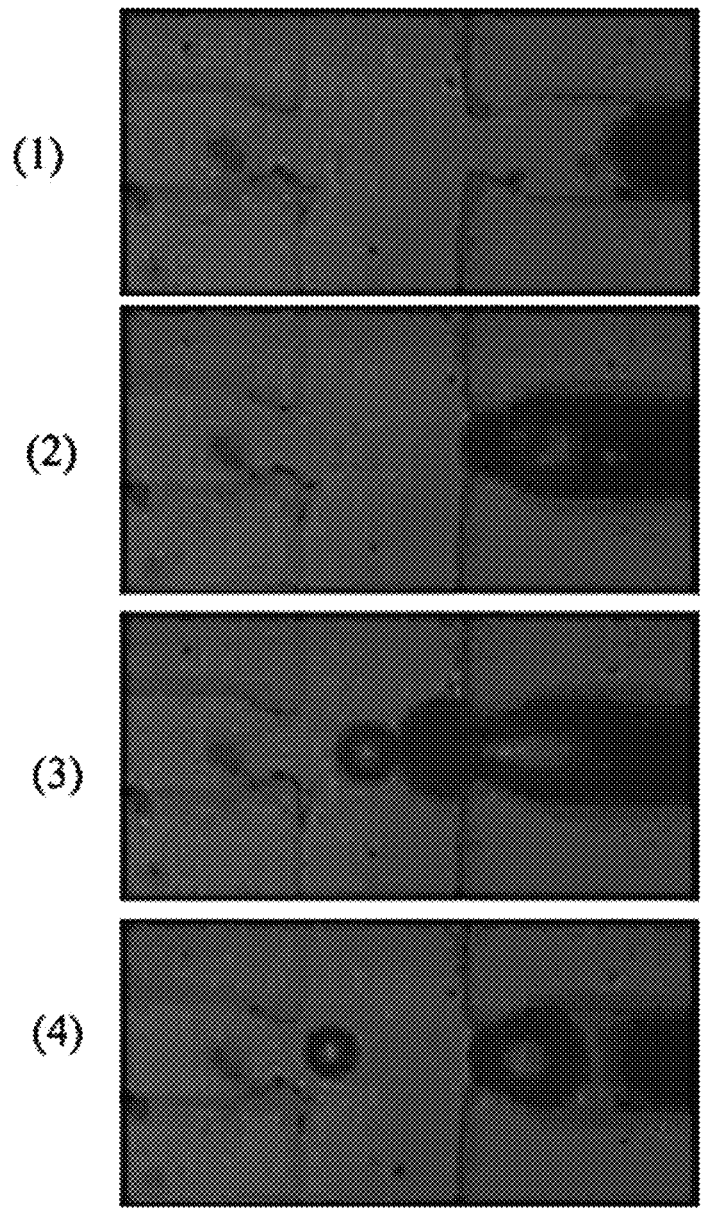
FIG. 14 is a photograph substituting for a drawing, and is a photograph of the generation of bubbles 36 captured by a high-speed camera in example 5.

FIG. 14 is a photograph of the generation of bubbles 36 captured by a high-speed camera. As is clear from the photograph, it was confirmed that bubbles 36 could be jetted from the bubble-jetting outlet 35 by using the bubble-jetting chip 1 produced in example 4, and that the jetted bubbles 36 reached the process-target-placement channel 72.

[Key]

1: Bubble-jetting chip 1, 2: Substrate, 3: Bubble-jetting portion, 4: Energizing portion, 5: Counter electrode, 6: Localized ablation device, 7: Injection solution channel, 8: First injection solution channel, 9: Second injection solution channel, 31: Electrode, 32: Extended section, 33: Insulating portion, 34: Space, 35: Bubble-jetting outlet, 36: Bubble, 37: Insulating layer, 38: Assist channel, 39: Pump connection part, 61: General commercial AC power supply device, 62: Electric wire, 63: Non-dielectric resistor, 64: High-voltage amplification circuit, 71: Insulating wall, 72: Process-target-placement channel, 81: Hole

What is claimed is:

1. A bubble-jetting chip, comprising:
    a substrate with two or more bubble jetting portions and two or more assist channels formed on the substrate;
    the bubble-jetting portions comprising:
    an electrode that is formed of a conductive material;
    an insulating portion formed of an insulating photosensitive resin that sandwiches the electrode and includes an extended section that extends beyond the tip of the electrode;
    a bubble-jetting outlet that is formed at the tip of the extended section; and a space that is formed between the extended section of the insulating portion and the tip of the electrode wherein the insulating portion is continuously formed from the section that sandwiches the electrode to the bubble-jetting outlet, the electrode is either formed on an energizing portion which is formed on the substrate or the electrode is formed on the substrate, and
    wherein at least one of the assist channel is formed in the insulation portion and is parallel with at least one of the adjacent bubble jetting portions.

2. The bubble-jetting chip according to claim 1, wherein the extended section is tapered.

3. The bubble-jetting chip according to claim 2, wherein the photosensitive resin is a negative photoresist.

4. The bubble-jetting chip according to claim 1, wherein the photosensitive resin is a negative photoresist.

5. The bubble-jetting chip according to claim 4, wherein an injection solution channel is formed around the bubble-jetting portion.

6. The bubble jetting chip according to claim 1, wherein the electrode is formed on the energizing portion which is formed on the substrate.

7. The bubble-jetting chip according to claim 1, wherein a counter electrode that constitutes an electrode pair with the electrode of the bubble-jetting portion is formed on the substrate.

8. The bubble jetting chip according to claim 1, wherein an injection solution channel is formed around the bubble-jetting portion.

9. The bubble jetting chip according to claim 1, wherein the substrate forms a part of the bubble-jetting outlet.

10. A localized ablation device, comprising the bubble-jetting chip according to claim 1.

11. An injection device, comprising the bubble-jetting chip according to claim 1.

12. A localized ablation device, comprising the bubble-jetting chip according to claim 4.

13. An injection device, comprising the bubble-jetting chip according to claim 4.

14. A localized ablation method, comprising:

injecting a solution so that a counter electrode has continuity with the electrode of the localized ablation device according to claim 10;

applying high-frequency pulses to the electrode of the localized ablation device and the counter electrode to cause bubbles to be ejected from the tip of the bubble-jetting portion; and processing a process target with the bubbles.

15. An injection method, comprising:

injecting a solution so that a counter electrode has continuity with the electrode of the injection device according to claim 11;

delivering a solution containing an injection material to the front of the bubble-jetting portion;

applying high-frequency pulses to the electrode of the injection device and the counter electrode to cause the ejection of bubbles onto which the solution containing the injection material is adsorbed; and introducing the injection material into a process target while localized ablation is performed on the process target with the bubbles.

* * * * *